United States Patent [19]
Scharf

[11] Patent Number: 5,139,188
[45] Date of Patent: *Aug. 18, 1992

[54] DENTAL DISPENSER FOR LIGHT CURABLE SUBSTANCES

[76] Inventor: Jonathan Scharf, 364-A7 Andrews Rd., Glenmoore, Pa. 19343

[*] Notice: The portion of the term of this patent subsequent to Feb. 12, 2008 has been disclaimed.

[21] Appl. No.: 630,645

[22] Filed: Dec. 20, 1990

Related U.S. Application Data

[63] Continuation-in-part of Ser. No. 499,239, Mar. 26, 1990.

[51] Int. Cl.⁵ .................... A41D 19/00; B65D 83/10
[52] U.S. Cl. .................................. 224/217; 224/218; 224/236; 206/368; 206/815
[58] Field of Search ............. 224/217, 218, 219, 236, 224/241; 206/368, 369, 370, 815

[56] References Cited

U.S. PATENT DOCUMENTS

| | | | |
|---|---|---|---|
| 1,199,635 | 9/1916 | Urmston | 224/218 |
| 4,463,879 | 8/1984 | Des Voignes | 224/217 X |
| 4,844,308 | 7/1989 | Porteous | 224/217 |

Primary Examiner—Henry J. Recla
Assistant Examiner—David J. Walczak
Attorney, Agent, or Firm—Michael F. Petock

[57] ABSTRACT

A dispenser for maintaining light sensitive substances utilized in the practice of dentistry shielded from light and providing easy and convenient access by the dentist includes a container and a cover therefor with the cover being hingedly attached to the container. The container includes wells for receiving one or more light sensitive substances. The container is provided with a finger hold or holds for maintaining the container on one or more digits of a hand. In one embodiment, the cover is connected to the container by a resilient hinge and the cover may be released from engagement with the container by pushing forward on the hinge side of the cover. The resilient hinge will cause the cover to automatically open. Accordingly, the dispenser may be held in one hand and readily opened and closed to provide easy, quick, convenient access to the light sensitive substances by the dentist. Other embodiments include a conventional pin type hinge, insert holes for the attaching of color matching tabs, a removable or permanent thumb strap on the cover, a removable insert or tray which is disposable or a completely disposable dispenser. The cover may be retained in engagement with the container by sealing lips or a separate latch.

26 Claims, 5 Drawing Sheets

DENTAL DISPENSER FOR LIGHT CURABLE SUBSTANCES

CROSS REFERENCE TO RELATED APPLICATION

This application is a continuation-in-part patent application of application Ser. No. 07/499,239 filed Mar. 26, 1990 for DENTAL DISPENSER FOR LIGHT CURABLE SUBSTANCES by the inventor herein. The benefit of the earlier filing date for common subject matter is hereby claimed and the subject matter of said parent application is incorporated herein by reference the same as if set forth at length.

BACKGROUND OF THE INVENTION

This invention is directed to an improved dental dispenser for light curable substances. More particularly, the invention relates to an improved dispenser which will shield light curable resins and the like from light and enable convenient use of the same as needed.

Light curable resins and the like have become widely utilized in the practice of dentistry. It is necessary that these substances be made available to the dentist as needed in performing the dental operation and shielded from light as much as possible. The light sensitive substances should be shielded from light not only during extended periods, but even during the multiple periods of time between when the dentist actually needs access to the light curable resin or the like during the dental operation.

U.S. Pat. No. 4,822,280-Rider discloses a dispenser for light curable substances wherein a box like dispenser is provided with a slidable lid for closing off the dispenser to isolate the light curable substance contained therein. This patent further discloses that the dispenser is provided with a syringe inserted into the side for the injection of the light curable substance into the container.

The present invention makes improvements over applicant's co-pending parent application referred to above.

SUMMARY OF THE INVENTION

In accordance with the present invention, a dental dispenser for light curable substances is provided which will not only shield the light curable substances from light, but which may be easily and efficiently held and operated by a single hand. In most dental offices today, the dentist usually employs a dental assistant for the purpose of aiding in the dental operation in the form of handing the dentist various instruments and materials as needed as well as suctioning and providing general assistance. Accordingly, typically the dental dispenser of the present invention will be utilized by the dental assistant, and will generally be described herein in that context, although it is understood that a dentist may utilize the present invention in one hand or that it may be used by any other person in a similar manner.

One of the advantages of the present invention is that it enables effective and convenient access by the dentist to the light curable substances, such as composite resins, while maintaining the light sensitive or curable substances shielded from light.

A further advantage of the present invention is that the light shielded light sensitive substances require only one hand of the dental assistant or other person, thereby enabling the other hand of the dental assistant to be utilized for various other purposes such as suctioning or the handing of instruments or other materials to the dentist.

A further advantage of the present invention is that it provides convenient storage of dental restorations, such as laboratory fabricated filling material and the like to be used by the dentist during the dental operation, as may be necessary.

Another advantage of the present invention is that it provides means for attaching color tabs to the dental dispenser which are useful in achieving color matches between restorted materials and the teeth of the patient being repaired.

In accordance with the present invention, the dental dispenser is in the form of a unitary container and cover both formed of a light opaque material with the cover sealably mating with the container to prevent the entry of light when the cover is in sealable engagement with the container. A releasable latch means is provided for maintaining the cover in sealably mating condition with the container. In one embodiment, the container and the cover are provided with a resilient hinge for allowing the cover to hingeably sealably mate with the container and to cause the cover to hingeably open when the latch means is released. The container is provided with means for retaining the container on one or more digits of the user's hand whereby the dispenser may be retained on and opened and closed by the digits of one hand.

Various other embodiments of the invention are illustrated, including but not limited to those with a removable thumb strap, a removable insert, a conventional hinge, means for attaching color tabs, and other variations and combinations thereof, the essence of which is illustrated herein.

The term digit as used herein is to be interpreted to include all five fingers, i.e. sometimes referred to as the four fingers and the thumb.

BRIEF DESCRIPTION OF THE DRAWINGS

For the purpose of illustrating the invention, there are shown in the drawings forms which are presently preferred; it being understood, however, that this invention is not limited to the precise arrangements and instrumentalities shown.

DETAILED DESCRIPTION OF THE PREFERRED EMBODIMENTS

Figure 1:
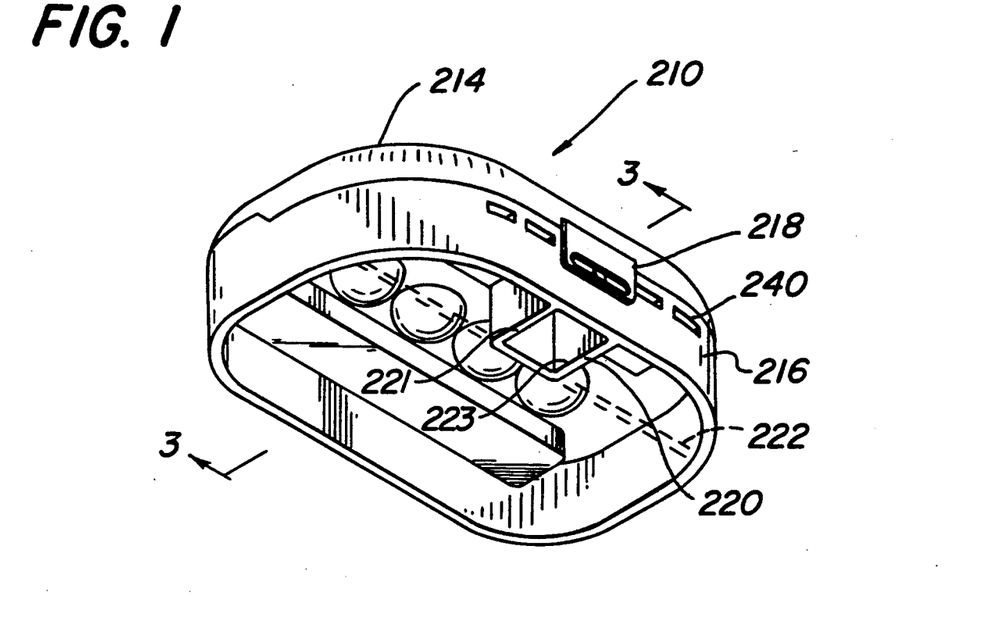
FIG. 1 is a view in perspective of a preferred embodiment of the present invention taken from the lower right, with the dental dispenser being shown in the closed condition.
Figure 2:
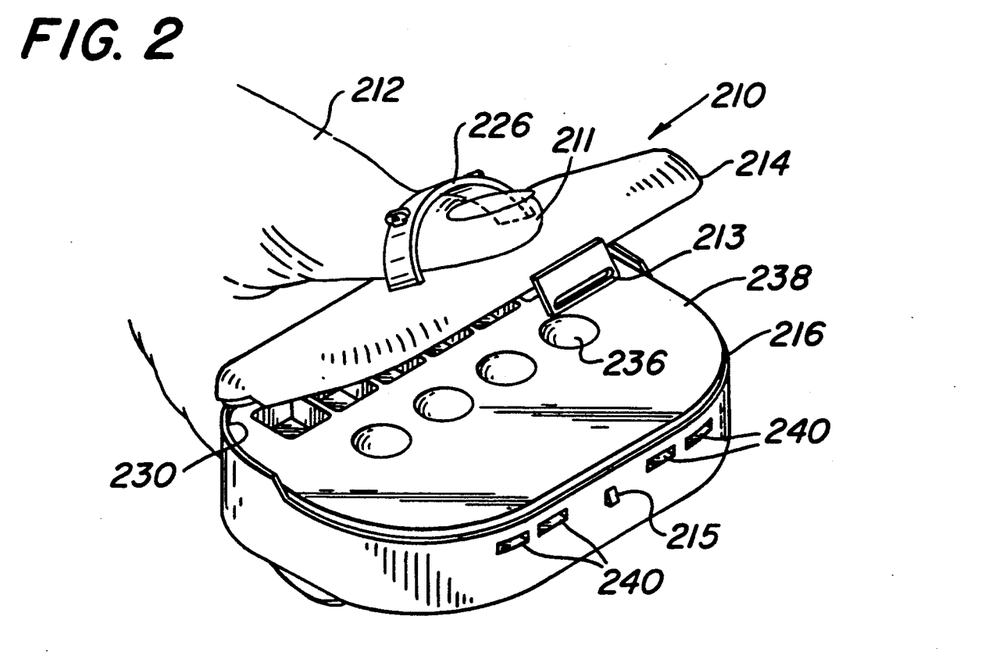
FIG. 2 is a view in perspective of the embodiment of the present invention shown in FIG. 1, in the partially open position, as it is held in the hand of a person.

Referring now to the drawings in detail, wherein like numerals indicate like elements, there is shown in FIG. 1 an improved dental dispenser 210 viewed from the right and from below. The same dental dispenser 210 is shown in a partially open condition in FIG. 2 held in one hand 212 of a person. This person may be a dental assistant. The fingers and the thumb of a person herein may be referred to interchangeably as digits, that is, either five digits of the hand, or as a thumb and forefingers. As shown in FIG. 2, the cover 214 of the dental dispenser may be controllably operated by the thumb 211 and other fingers of the hand 212 would be utilized on the bottom of container 216 to hold and control dental dispenser 210. However, it is understood that this manner of holding the dental dispenser could be reversed without in any way affecting the teachings herein or the scope of the present invention. For example, one of the fingers such as the forefinger or middle finger could be inserted through loop 226 instead of the thumb, and the thumb could be used on the bottom of container 216 to control the dental dispenser.

Continuing to refer to FIGS. 1 and 2, there is shown a cover 214 and a container 216. The cover 214 is provided with a latch 218. The latch may be comprised of a latch member 213 mounted on cover 214 which engages a projection 215 on container 216.

As may be seen most clearly on FIG. 1, the lower portion of container 216 is hollow, and is provided with one or more finger holes 220. Finger hole 220 may be comprised of a single square or rectangular formation at 220 for the insertion of a single finger or it may be comprised of a wall shown in dotted lines at 222 against which pressure may be applied by a plurality of fingers, with or without sidewalls 221 and 223.

Figure 3:
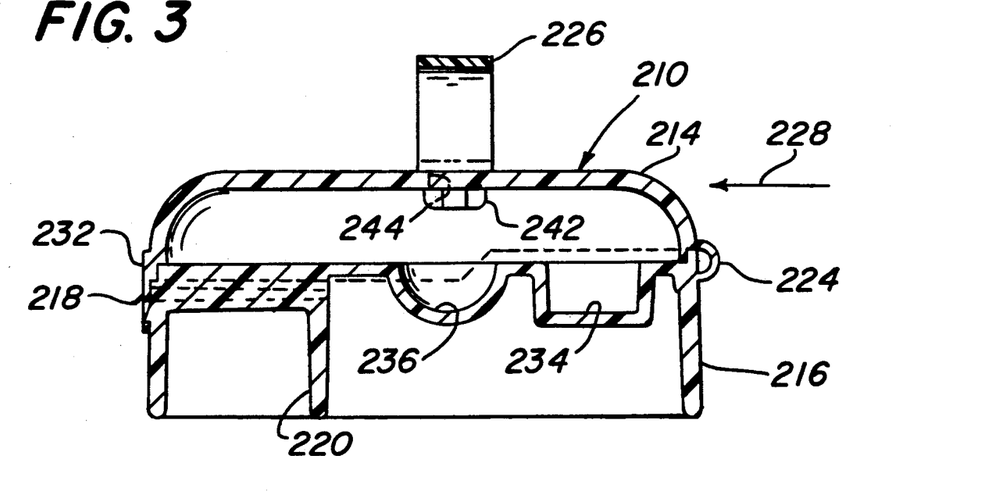
FIG. 3 is a cross sectional view taken along line 3—3 of FIG. 1.
Figure 4:
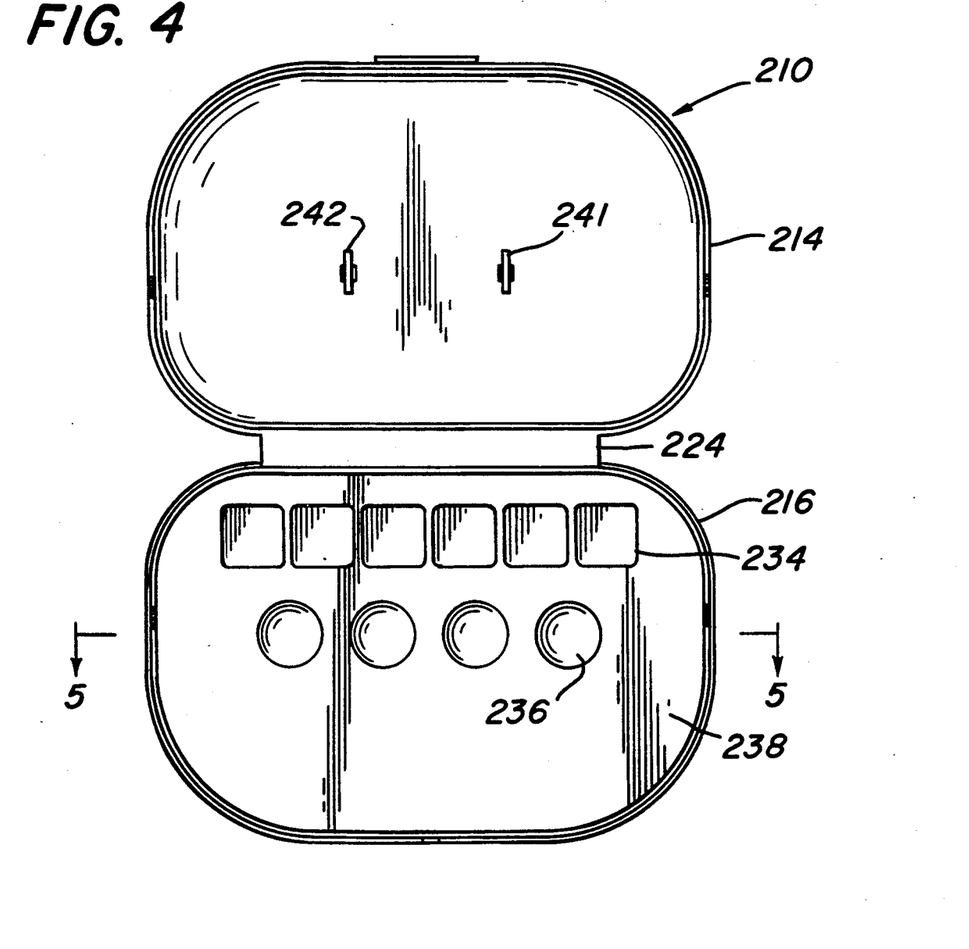
FIG. 4 is a plan view of the embodiment shown in FIGS. 1 and 2 with the cover of the container completely open.

Referring now to FIGS. 3 and 4 taken in conjunction with FIGS. 1 and 2, FIG. 3 is a cross sectional view of the dental dispenser 210 taken along line 3—3 of FIG. 1. FIG. 4 is a plan view of dental dispenser 218 with cover 214 completely open. FIG. 4 illustrates the form in which the container may be molded as a unit from various well known light opaque synthetic plastic materials, such as polypropylene, by well known molding technology. Of course other synthetic materials in addition to polypropylene may be utilized. As is well known, composite resins may be utilized, particularly those containing carbon black for example, to provide the desired degree of opaqueness or resistance to light, including ultraviolet light radiation. The molding of the dental dispenser in this manner produces a resilient hinge 224 which tends to force cover 214 to the completely open position when latch 218 is released, as shown in FIG. 4.

As may be best seen by viewing FIG. 3 in conjunction with FIG. 2, dental dispenser 218 may be conveniently operated by one hand of the dental assistant by being held substantially as illustrated in FIG. 2 with thumb 211 passing through thumb strap 226 on cover 214 and one or more fingers inserted in the finger holes in the lower portion of container 216. Cover 214 is normally held in a closed position by latch 218 as illustrated in FIG. 1. By applying pressure to the rear side or hinge side of cover 214 substantially in the horizontal direction of arrow 228, cover 214 is caused to move forward, i.e. in the direction of arrow 228, causing latch 218 to release, by reason of latch member 213 becoming disengaged from projection 215, thereby allowing cover 214 to open by reason of the resiliency of hinge 224. A cover partially opening is illustrated in FIG. 2. This operation is enabled by the construction of the seal between container 216 and cover 214 as best illustrated in FIGS. 1, 2 and 3. As illustrated therein, the container has a raised lip 230 in the rear portion and cover 214 has a downwardly projecting lip 232 along its front. As illustrated in the figures, the downwardly projecting front lip 232 extends for a distance backwardly along each side to a point where it meets the upwardly projecting lip 230 of the container. This junction point may be selected at various points along the side of dental dispenser 210. Lips 230 and 232 form a light-tight seal when dental dispenser 210 is closed.

As may be seen from the figures, wells 236 are provided. Wells 236 may be utilized for the storage of composite light sensitive resins and may be referred to herein as composite resin wells although it is understood that other types of materials including liquids and etchants utilized in the dental operation may be stored in wells 236. Additionally, container 216 is provided with compartments 234 which may be square as illustrated or any other suitable shape. Compartments 234 may preferably be utilized for the storage of dental restorations such as laboratory fabricated filling material and dental inserts, such as caps and the like. However, compartments or wells 234 may be utilized as desired by the dentist. The wells 236 and the compartments 234 may be arranged in various numbers and in various formats. However, the arrangement as illustrated in FIG. 4 is a currently preferred embodiment of the present invention. The forward upper portion of the container is a flat surface 238 which may be utilized by the dentist in a manner similar to a palette for the mixing of the resins as may be necessary.

The compartments or square wells 234 utilized for the storage of dental restorations provide a significant advantage in that the dental restorations may be coated with light curable resins and protected from light until placement in the mouth of the dental patient. This is particularly important where the dentist may be utilizing a plurality of dental restorations, thereby enabling the precoating of all the dental restorations with a light curable resin and being able to store them in wells or compartments 234 enabling the placement of all of the dental restorations at one time without curing.

In a presently preferred embodiment, the front of dental dispenser 210 is provided with a plurality of insert holes 240 which may be used to receive inserts on color tabs which are utilized by the dentist for color matching.

Figure 5:
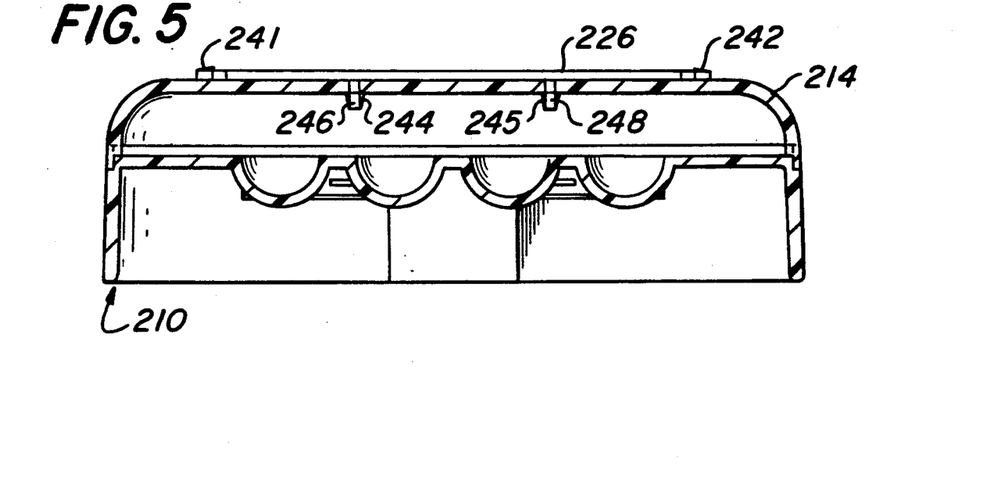
FIG. 5 is a cross sectional view which would correspond to a view taken substantially along line 5—5 of FIG. 4 with the cover closed and the thumb strap stored on the cover.
Figure 6:
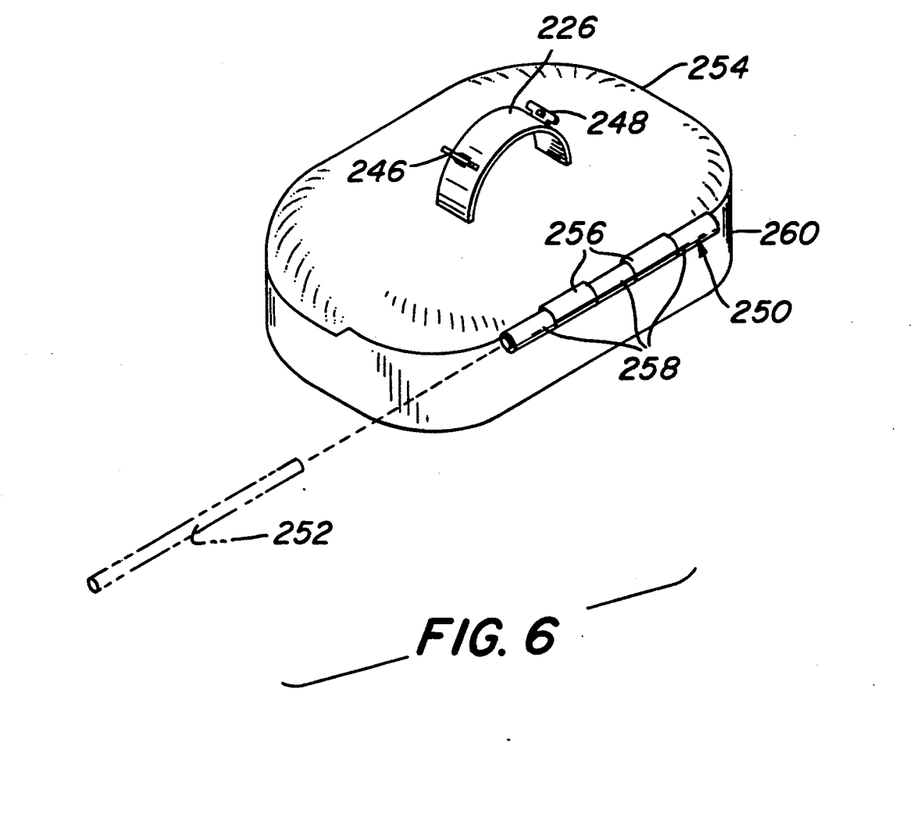
FIG. 6 is a view in perspective of another embodiment of the present invention illustrating another type of hinge.

As may be better illustrated by considering FIGS. 5 and 6 in conjunction with the previously discussed FIGS. 1 through 4, thumb strap 226 is removable and may be utilized as an option by the dentist or dental assistant. As may be best seen in FIG. 3, dental strap 226 is provided at each end with attachment tabs 241, 242 which lock into holes 244 in cover 214 for enabling thumb strap 226 to be utilized as a thumb hole or holder. If it is desired to use the dental dispenser 210 without a thumb hole or thumb holder for cover 214, tabs 246 and 248 mounted intermediate of the ends of thumb strap 226 may be used to secure thumb strap 226 in place by the insertion of attachment tabs 246 and 248 into holes 244 and 245 of cover 214. The tabs 246 and 248 also perform the function of sealing holes 244 and 245 if the use of thumb strap 226 as a thumb holder is not desired.

It may be noted that FIG. 4 may be used to illustrate the interior view of cover 214 for thumb strap 226 either in the used or stored condition.

With respect to the tabs 241, 242, 244, 248 and the thumb strap tabs illustrated in the other embodiments of the invention in this application, any suitable type of attachment tab may be utilized, as is well known in the art. The tabs illustrated in the drawings are illustrated as providing retaining means in two orthogonal directions. The provision of retaining means on the tabs in a single plane would be sufficient and other types of attachment tabs may be utilized as is well known in the art.

FIG. 6 also illustrates another embodiment of a hinge 250 which may be utilized in the practice of the present invention. Hinge 250 does not provide the resilient function, but is a conventional hinge structure which may be utilized in practicing the invention. When hinge 250 is utilized, thumb strap 226 becomes more desirable as a means of opening the cover which has been designated in FIG. 6 as 254. Hinge 250 is comprised of pin 252 which is mounted through pin receiving members 256 on cover 254 and pin receiving members 258 on container 260. The dispenser illustrated in FIG. 6 may be fabricated from ABS, polypropylene or any other suitable resin. Pin 252 may be constructed of a suitable synthetic resin such as ABS, stainless steel or any other suitable relatively rigid material that is well known in the art.

Figure 7:
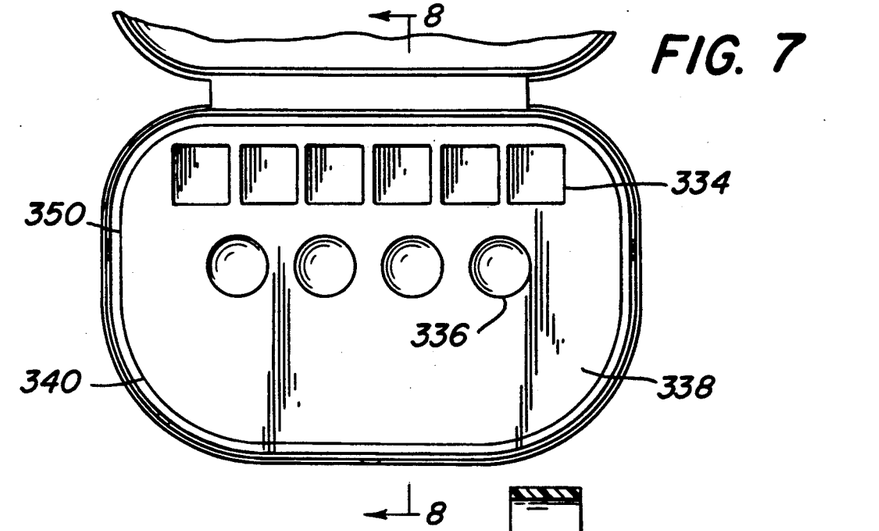
FIG. 7 is a plan view of another embodiment of the present invention with the cover open illustrating a removable insert tray for the composite resin.
Figure 8:
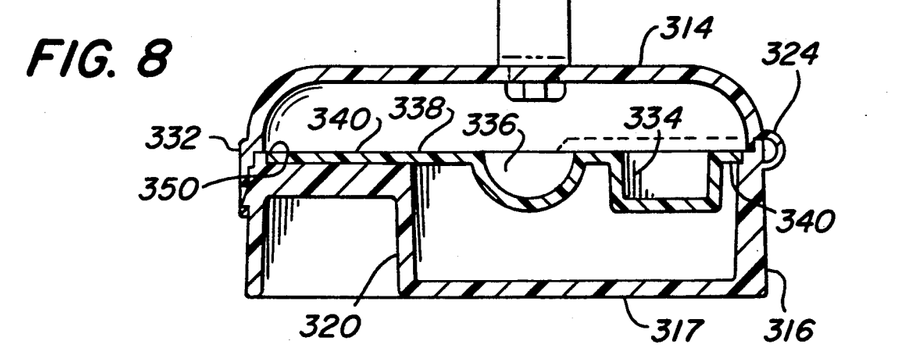
FIG. 8 is a cross sectional view taken substantially along line 8—8 of FIG. 7 with the cover of the dental dispenser being closed.

Referring now to FIGS. 7 and 8, there is shown another embodiment of the present invention wherein wells 334 and 336 and palette 338 are formed on a removable insert 340. The square wells 334 and the round wells 336 may be utilized for the same functions as described with respect to the wells of the previous embodiments. Removable insert 340 may be disposable. As may be seen in FIG. 8, container 316 is provided with a bottom 317 and finger insert or inserts 320. Cover 314 is connected to container 316 by a hinge 324 which may be a resilient hinge as illustrated, a hinge similar to hinge 258 or any other suitable type of hinge. Lip structure 332 on cover 314 and the lip structure on container 316 may be the same as described with respect to FIGS. 1 through 4. Removable insert 340 in which wells 336 and 334 are formed fits within a mating receiving structure formed in container 316. The outer rim of insert 340 is shown at 350 in FIGS. 7 and 8.

Although the embodiment shown in FIGS. 7 and 8 is illustrated with a flexible resilient hinge, it is understood that that embodiment could and, would be just as likely, to utilize the pin hinge illustrated in FIG. 6. It is contemplated in the embodiment of FIGS. 7 and 8 that the removable insert 340 may be more preferably fabricated from ABS (Acrylonitrile-Butadiene-Styrene) resin which is rigid and more chemically resistant than polypropylene. With the pin type hinge of FIG. 6, the entire dental dispenser may be molded from ABS or any other suitable well known resin.

Figure 9:
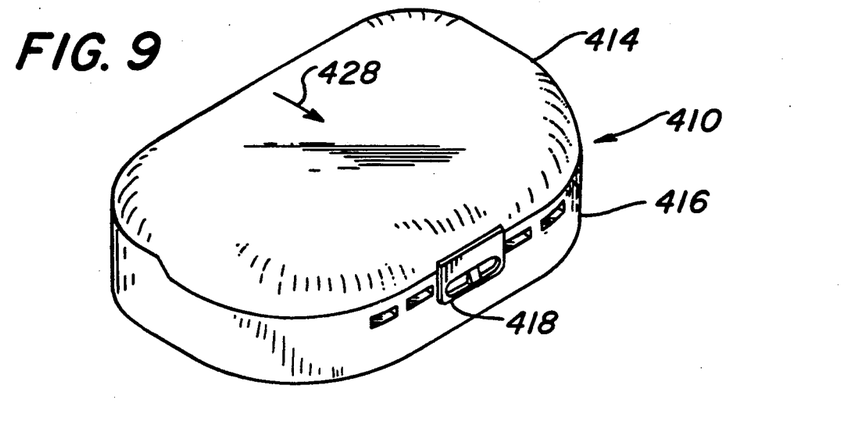
FIG. 9 is a view in perspective of another embodiment of the present invention which does not utilize a thumb strap nor mounting holes therefor in the cover.

There is shown another embodiment in FIG. 9 of a dental dispenser 410 having a cover 414 and a container 416. Dental dispenser 410 may be similar to the various other embodiments with the exception that the cover 414 is not provided with a thumb strap nor holes for receiving a thumb strap. Dental dispenser 410 as illustrated in FIG. 9 is to be held by the fingers in finger holes on the undersurface of container 416 by being pressed backwardly so that the back surface of dental dispenser 410 engages the ball of the thumb. Dental dispenser 410 is provided with a resilient hinge, thereby enabling the cover to be opened by pressing forward, i.e. in the direction of arrow 428, to release latch 418. With latch 418 released, cover 414 would springably open. The dental dispenser may be closed by forcing downwardly on cover 414 by means of the thumb.

Figure 10:
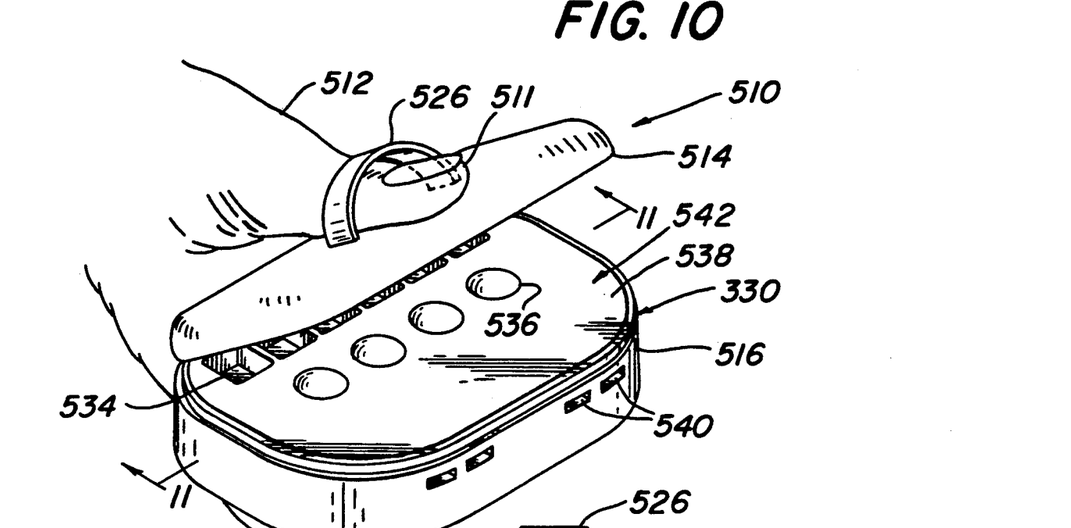
FIG. 10 is a view in perspective of another embodiment of the present invention illustrating a dental dispenser with a disposable insert, a permanent thumb strap and wherein the cover may be retained by means of mating lip structure between the cover and the container.
Figure 11:
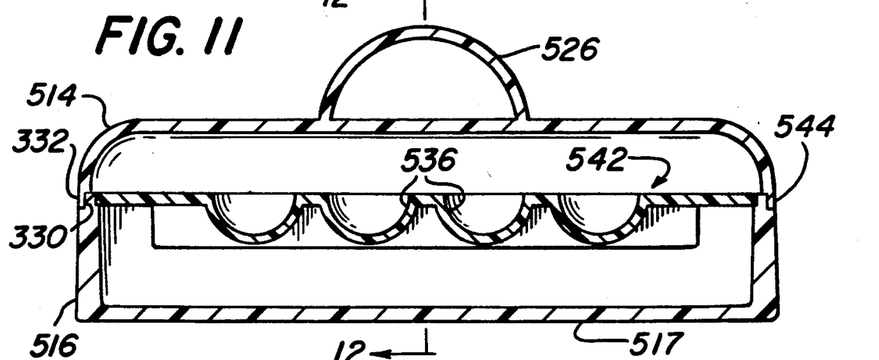
FIG. 11 is a cross section view taken along line 11—11 of FIG. 10 with the cover of the dental dispenser being closed.
Figure 12:
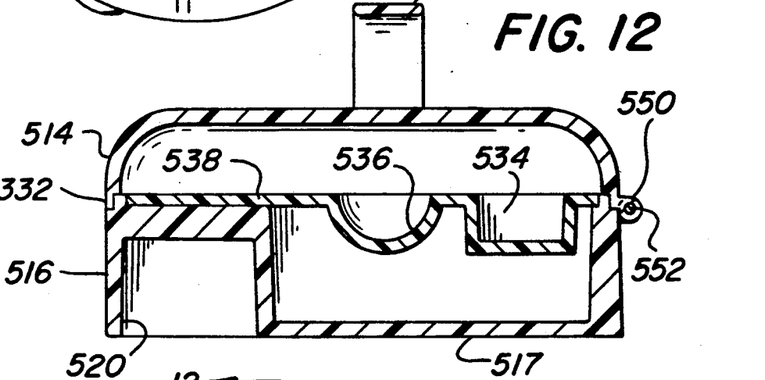
FIG. 12 is a cross sectional view in perspective taken along line 12—12 of FIG. 11.

Referring now to the embodiment illustrated in FIGS. 10, 11 and 12 there is shown a dental dispenser 510 having a mating lip structure 330, 332 disposed substantially in a single plane which also comprises a locking structure, a disposable insert or tray 542 and a permanent thumb strap 526. Referring more specifically to FIGS. 10, 11 and 12, collectively, there is shown a dental dispenser 510 comprised of a container 516 with a cover 514 hingeably attached thereto by means of hinge 550. Hinge 550 is preferably illustrated to be a pin type hinge having a pin 552. However, it is understood that other suitable hinge structures may be utilized.

Cover 514 is sealably mated with container 516 when the container is closed as illustrated in FIGS. 11 and 12 by mating lips 330 on container 516 and 332 on cover 514. In this embodiment, since there is not a resilient hinge, a separate locking mechnamism is not required and the frictional engagement between the mating lips 330 and 332 is sufficient to maintain cover 514 in a closed condition. Further, since there is no need to force cover 514 forward, there is no need for the raised and lowered or reversing lip structure as discussed with respect to certain of the other embodiments.

As illustrated, dental dispenser 510 may be held in the hand of a dental assistant or other person with thumb 511 inserted within thumb strap 526. Thumb strap 526 is molded as a part of or on cover 514 and is permanently attached thereto. A finger hold is illustrated on the lower surface of container 516 at 520. This structure may be similar to the other embodiments disclosed, providing a finger hold for a single finger or a plurality of fingers. Container 516 is provided with a bottom structure 517.

Removable insert tray 542 is provided with wells 536 and 534. Wells 536 and 534 may be utilized as described with respect to the wells in the other embodiments, wells 536 being provided preferably for composite resins, etchant materials and other dental substances or liquids utilized in the dental operation. Storage wells or compartments 534 may be utilized for the storage of dental restorations as described previously. Area 538 serves as a palette. Insert 542 is preferably disposable, although it may be merely removable for cleaning and reinsertion. Insert 542 is matingly received within container 516 as described with respect to the previous embodiments. Particularly, insert 542, as best illustrated in FIGS. 11 and 12, may sit in a recess 544 formed in the upper rim of container 516. Of course, other suitable means may be utilized to matingly mount insert 542 in container 516.

As with the other embodiments, this embodiment, including the disposable insert 542, of of FIGS. 10-12 may be molded from any suitable material, including ABS, polypropylene or any other light opaque suitable materials.

In view of the above, the present invention may be embodied in other specific forms without departing from the spirit or essential attributes thereof and, accordingly, reference should be made to the appended claims, rather than to the foregoing specification as indicating the scope of the invention.

I claim:

1. Apparatus for use in the practice of dentistry, comprising:
   a container and a cover, both formed of a light opaque material, said cover sealably mating with said container to prevent the entry of light when said cover is in sealable engagement with said container;
   one or more wells for receiving light sensitive substances utilized in the practice of dentistry;
   a resilient hinge for allowing said cover to hingeably sealably mate with said container;
   a releasable latch for maintaining said cover in sealably mating condition with said container;
   said container being provided with means for enabling retention of said container on a user's hand, said means including means for receiving one or more digits of a user's hand; and
   whereby said apparatus may be retained on and opened and closed by the digits of one hand.

2. Apparatus in accordance with claim 1 wherein said releasable latch includes structure on the cover and container in an area opposite said, hinge such that pressure on said cover near said hinge releases said latch allowing the cover to hingeably open.

3. Apparatus in accordance with claim 2 wherein said cover is in sealable engagement with said container by means of a lip extending downwardly from said cover along at least the hinge side of said cover and a lip extending upwardly along at least a side of said container provided with said latch means.

4. Apparatus in accordance with claim 1 wherein said cover is provided with a strap for receiving a digit.

5. Apparatus in accordance with claim 4 wherein said strap on said cover is removably attached to said cover.

6. Apparatus in accordance with claim 5 wherein said strap on said cover is removably attached to said cover by means of tabs located on the ends of said strap which are insertable into holes formed a predetermined distance apart in said cover.

7. Apparatus in accordance with claim 6 wherein said strap may be stored on said cover, said strap being provided with two additional tabs spaced a distance equal to the distance between the holes in the cover, whereby said two additional tabs may be inserted into the holes in the cover causing said strap to be stored on said cover.

8. Apparatus in accordance with claim 1 wherein said container is provided with one or more means for attaching color matching tabs.

9. Apparatus in accordance with claim 8 wherein said attachment means comprise insert holes formed in said container, said holes not passing to the interior of said container.

10. Apparatus in accordance with claim 1 including one or more compartments for receiving dental restorations.

11. Apparatus in accordance with claim 10 wherein said container is provided with a removable insert in which said wells and compartments are formed.

12. Apparatus in accordance with claim 1 wherein said container is provided with a removable insert in which said wells are formed.

13. Apparatus for use in the practice of dentistry, comprising:
   a container and a cover, both formed of a light opaque material, said cover sealably mating with said container to prevent the entry of light when said cover is in sealable engagement with said container;
   means for releasably maintaining said cover in sealably mating condition with said container;
   a hinge for allowing said cover to hingeably sealably mate with said container and to cause said cover to hingeably open when said means for releasably maintaining is released;
   said container being provided with means for retaining said container on one or more digits of a user's hand; and
   whereby said apparatus may be retained on and opened and closed by the digits of one hand.

14. Apparatus in accordance with claim 13 wherein said means for releasably maintaining said cover is comprised of mating lip structures on an upper perimeter of the container and a lower perimeter of said cover.

15. Apparatus in accordance with claim 13 wherein said means for releasably maintaining said cover includes structure on the cover and container in an area opposite said hinge such that pressure on said cover releases the cover to hingeably open.

16. Apparatus in accordance with claim 13 wherein said container is adapted to store light sensitive substances in the form of composite resins utilized in the practice of dentistry.

17. Apparatus in accordance with claim 13 wherein said retaining means of said container is comprised of one or more openings formed in a lower surface of said container for insertion of one or more digits, said opening or openings being sealed to prevent the entry of light into said container.

18. Apparatus in accordance with claim 13 wherein said container is provided with one or more means for attaching color matching tabs.

19. Apparatus in accordance with claim 18 wherein said attachment means comprise insert holes formed in said container, said holes not opening into said container.

20. Apparatus in accordance with claim 13 wherein said cover is provided with a removable thumb strap.

21. Apparatus in accordance with claim 13 wherein said cover is provided with a permanent thumb strap.

22. Apparatus in accordance with claim 13 wherein said hinge is comprised of a strip of resilient material connecting said container and said cover.

23. Apparatus in accordance with claim 13 wherein said hinge is comprised of two receiving members formed on said cover and pin receiving members received on said container with a single pin passing through both of said pin retaining members.

24. Apparatus in accordance with claim 13 including one or more compartments for receiving dental restorations.

25. Apparatus in accordance with claim 24 wherein said container is provided with a removable insert in which wells and said compartments are formed.

26. Apparatus in accordance with claim 13 wherein said container is provided with a removable insert in which wells are formed.

* * * * *

UNITED STATES PATENT AND TRADEMARK OFFICE
CERTIFICATE OF CORRECTION

PATENT NO. : 5,139,188

DATED : August 18, 1992

INVENTOR(S) : Jonathan Scharf

It is certified that error appears in the above-identified patent and that said Letters Patent is hereby corrected as shown below:

On the Title page, item [57], Abstract, col. 2, line 5, delete "hingedly" and substitute therefor --hingebly--.

Column 7, line 3, claim 2, delete ",".
        line 4, claim 2, after "on", insert --the hinge side of--.

Column 8, line 38, claim 15, after "on", insert --the hinge side of--.
        line 5, claim 15, before "releases", insert --near said hinge--.

Signed and Sealed this

Twenty-eighth Day of September, 1993

Attest:

BRUCE LEHMAN

Attesting Officer

Commissioner of Patents and Trademarks